(12) United States Patent
Christ

(10) Patent No.: US 8,394,906 B2
(45) Date of Patent: Mar. 12, 2013

(54) OPHTHALMIC LENS HAVING A YELLOW DYE LIGHT BLOCKING COMPONENT

(75) Inventor: Marie Dvorak Christ, Laguna Beach, CA (US)

(73) Assignee: Aaren Scientific Inc., Ontario (CA)

( * ) Notice: Subject to any disclaimer, the term of this patent is extended or adjusted under 35 U.S.C. 154(b) by 364 days.

(21) Appl. No.: 12/867,226

(22) PCT Filed: Feb. 11, 2009

(86) PCT No.: PCT/US2009/000891
§ 371 (c)(1),
(2), (4) Date: Aug. 11, 2010

(87) PCT Pub. No.: WO2009/102454
PCT Pub. Date: Aug. 20, 2009

(65) Prior Publication Data
US 2010/0296051 A1 Nov. 25, 2010

Related U.S. Application Data

(60) Provisional application No. 61/028,088, filed on Feb. 12, 2008.

(51) Int. Cl.
*C08F 26/06* (2006.01)
(52) U.S. Cl. ........................................................... 526/261
(58) Field of Classification Search ................... 526/261
See application file for complete search history.

(56) References Cited

U.S. PATENT DOCUMENTS

| | | | |
|---|---|---|---|
| 2,784,204 A * | 3/1957 | Heyna et al. .................. | 564/433 |
| 5,433,746 A | 7/1995 | Namdaran et al. | |
| 5,617,154 A | 4/1997 | Hoffman | |
| 5,628,798 A | 5/1997 | Eggleston et al. | |
| 5,662,707 A * | 9/1997 | Jinkerson ..................... | 623/6.17 |
| 5,693,095 A | 12/1997 | Freeman et al. | |
| 5,770,637 A | 6/1998 | Vanderlaan et al. | |
| 5,846,457 A | 12/1998 | Hoffman | |
| 5,891,931 A | 4/1999 | LeBoeuf et al. | |
| 5,922,821 A | 7/1999 | LeBoeuf et al. | |
| 5,968,094 A | 10/1999 | Werblin et al. | |
| 6,015,842 A | 1/2000 | LeBoeuf et al. | |
| 6,140,438 A | 10/2000 | Ojio et al. | |
| 6,158,862 A | 12/2000 | Patel et al. | |
| 6,187,042 B1 | 2/2001 | Sheets, Jr. et al. | |
| 6,210,438 B1 | 4/2001 | Sheets, Jr. et al. | |
| 6,242,551 B1 | 6/2001 | Tsuzuki et al. | |
| 6,244,707 B1 | 6/2001 | Faubl | |
| 6,277,940 B1 | 8/2001 | Niwa et al. | |
| 6,305,801 B1 | 10/2001 | Kerns, Jr. et al. | |
| 6,310,215 B1 | 10/2001 | Iwamoto | |
| 6,313,187 B2 | 11/2001 | LeBoeuf et al. | |
| 6,320,008 B2 | 11/2001 | Tsuzuki et al. | |
| 6,326,448 B1 | 12/2001 | Ojio et al. | |
| 6,353,069 B1 | 3/2002 | Freeman et al. | |
| 6,359,024 B2 | 3/2002 | Lai | |
| 6,465,538 B2 | 10/2002 | Lai | |
| 6,528,602 B1 | 3/2003 | Freeman et al. | |

(Continued)

FOREIGN PATENT DOCUMENTS

JP 01299560 A * 12/1989

OTHER PUBLICATIONS

European Search Report dated May 17, 2011.

*Primary Examiner* — Ling Choi
*Assistant Examiner* — Lanee Reuther
(74) *Attorney, Agent, or Firm* — Sheldon Mak & Anderson

(57) ABSTRACT

The invention is a polymeric ophthalmic lens material comprising a polymeric ophthalmic lens material comprising a) one or more lens-forming polymerizable monomers selected from the group of hydrophilic acrylate-substitute monomers, hydrophobic acrylate-substituted monomers, vinyl-substituted monomers, and platinum-catalyzed vinyl hydride addition-cured silicones, b) a polymerizable ultraviolet absorber and c) a polymerizable yellow dye. In one embodiment of the invention, the polymerizable ultraviolet absorber has the formula:

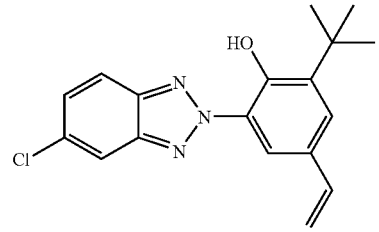

Figure 1:
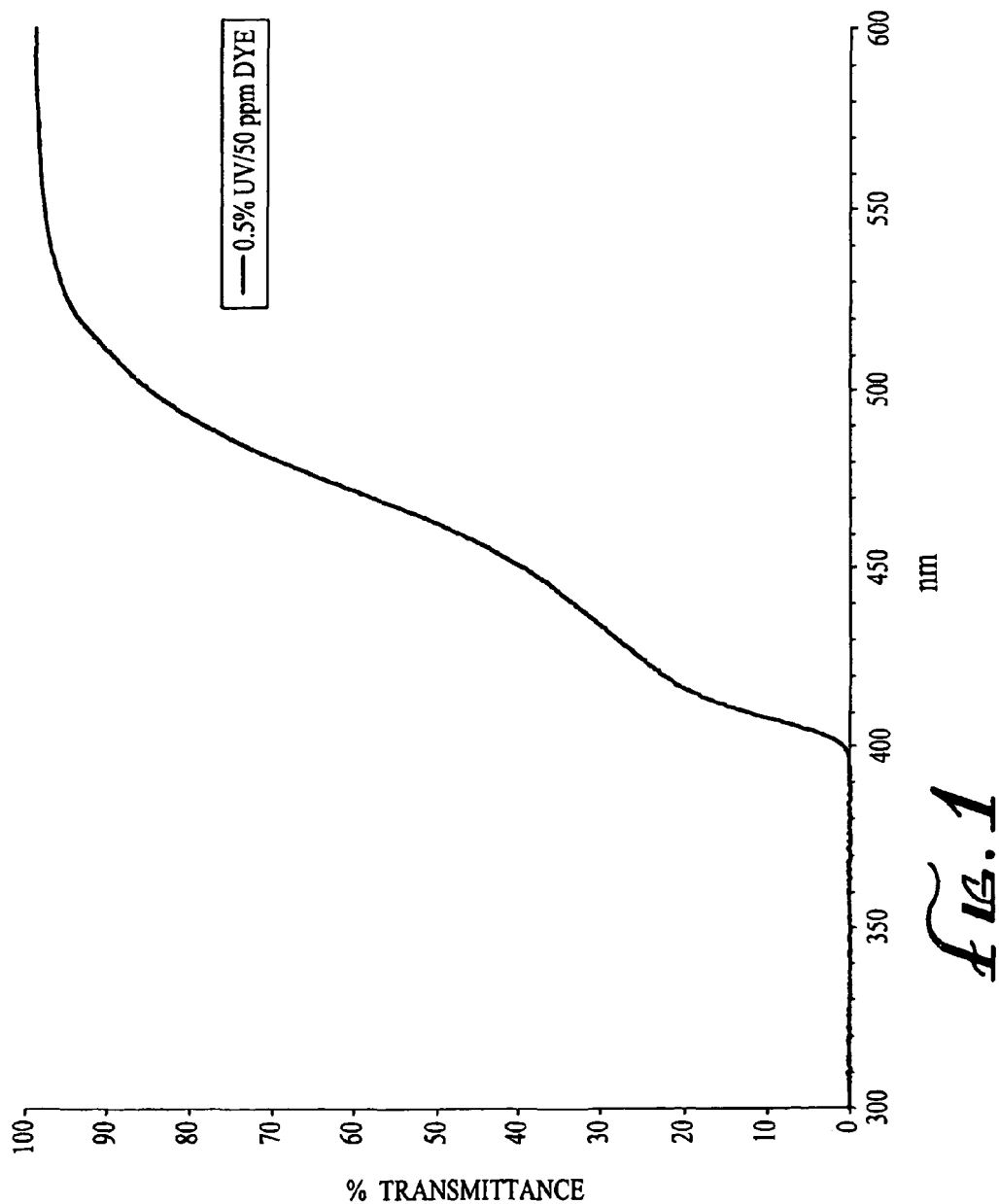

and the polymerizable yellow dye has the formula:

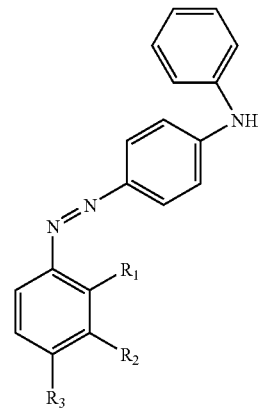

wherein $R_1$=vinyl, $R_2$, $R_3$=H, alkyl, hydroxyalkyl, wherein $R_2$=vinyl, $R_1$, $R_3$=H, alkyl, hydroxyalkyl, and wherein $R_3$=vinyl, $R_1$, $R_2$=H, alkyl, hydroxyalkyl.

12 Claims, 2 Drawing Sheets

U.S. PATENT DOCUMENTS

| | | |
|---|---|---|
| 6,586,508 B1 | 7/2003 | Ooga et al. |
| 6,638,991 B2 | 10/2003 | Baba et al. |
| 6,653,422 B2 | 11/2003 | Freeman et al. |
| 6,703,466 B1 | 3/2004 | Karakelle et al. |
| 6,806,337 B2 | 10/2004 | Schlueter et al. |
| 6,825,975 B2 | 11/2004 | Gallas |
| 6,846,900 B2 | 1/2005 | Ooga et al. |
| 6,852,780 B2 | 2/2005 | Fujita et al. |
| 6,872,793 B1 | 3/2005 | Schlueter |
| 6,878,792 B2 | 4/2005 | Ichinohe |
| 6,918,931 B2 | 7/2005 | Lai et al. |
| 6,926,405 B2 | 8/2005 | Ambler et al. |
| 6,955,430 B2 | 10/2005 | Pratt |
| 6,979,083 B2 | 12/2005 | Kerns, Jr. et al. |
| 6,984,038 B2 | 1/2006 | Ishak |
| 7,029,118 B2 | 4/2006 | Ishak |
| 7,033,391 B2 | 4/2006 | Lai et al. |
| 7,060,095 B2 | 6/2006 | Ho et al. |
| 7,098,283 B2 | 8/2006 | Lai |
| 7,119,210 B2 | 10/2006 | Schlueter |
| 7,150,760 B2 | 12/2006 | Zhang |
| 7,157,538 B2 | 1/2007 | Callaghan et al. |
| 7,208,012 B2 | 4/2007 | Callaghan et al. |
| 7,241,312 B2 | 7/2007 | Lai et al. |
| 7,278,737 B2 | 10/2007 | Mainster et al. |
| 7,304,117 B2 | 12/2007 | Lai |
| 7,326,423 B2 | 2/2008 | Pearson et al. |
| 7,354,980 B1 | 4/2008 | Mentak |
| 7,381,806 B2 | 6/2008 | Speckbacher et al. |
| 7,396,942 B2 | 7/2008 | Schuleter |
| 7,407,992 B2 | 8/2008 | Liao |
| 7,520,608 B2 | 4/2009 | Ishak et al. |
| 7,540,609 B2 | 6/2009 | Chen et al. |
| 7,556,376 B2 | 7/2009 | Ishak et al. |
| 7,652,076 B2 | 1/2010 | Schlueter et al. |
| 7,659,325 B2 | 2/2010 | Hagting et al. |
| 7,677,725 B2 | 3/2010 | Piers et al. |
| 7,691,917 B2 | 4/2010 | Lai et al. |
| 7,709,652 B2 | 5/2010 | Schlueter |
| 7,728,051 B2 | 6/2010 | Weinschenk, III et al. |
| 7,763,682 B2 | 7/2010 | Lowery et al. |
| 2005/0143812 A1 | 6/2005 | Paul et al. |
| 2005/0283234 A1 | 12/2005 | Zhou et al. |
| 2006/0142528 A1* | 6/2006 | Jethmalani et al. ............ 528/31 |
| 2006/0252844 A1 | 11/2006 | Mentak |
| 2006/0282163 A1 | 12/2006 | Schlueter et al. |
| 2007/0010883 A1* | 1/2007 | Mentak ..................... 623/6.58 |
| 2007/0055369 A1 | 3/2007 | Grubbs et al. |
| 2008/0182957 A1 | 7/2008 | Pearson et al. |
| 2008/0200983 A1 | 8/2008 | Bernard et al. |
| 2008/0242818 A1 | 10/2008 | Benz et al. |
| 2008/0266519 A1 | 10/2008 | Schlueter |
| 2009/0005864 A1 | 1/2009 | Eggleston |
| 2009/0088839 A1 | 4/2009 | Hu et al. |
| 2009/0118828 A1 | 5/2009 | Altmann |
| 2009/0164009 A1 | 6/2009 | Hu et al. |
| 2009/0232871 A1 | 9/2009 | Hitz et al. |
| 2009/0240329 A1 | 9/2009 | Gousse |
| 2009/0247661 A1 | 10/2009 | Muller-Lierheim et al. |
| 2009/0316246 A1 | 12/2009 | Asai et al. |
| 2010/0041787 A1 | 2/2010 | Chen |
| 2010/0085534 A1 | 4/2010 | Mainster et al. |
| 2010/0160482 A1 | 6/2010 | Nachbaur |
| 2010/0168438 A1 | 7/2010 | Schlueter |

\* cited by examiner

OPHTHALMIC LENS HAVING A YELLOW DYE LIGHT BLOCKING COMPONENT

CROSS-REFERENCE TO RELATED APPLICATION

The present Application is a 371 of International Patent Application No. PCT/US2009/000891, filed Feb. 11, 2009, entitled "Ophthalmic Lens Having A Yellow Dye Light Blocking Component," which claims the benefit of U.S. provisional patent application 61/028,038, filed Feb. 12, 2008, entitled "Intraocular Lens With UV Absorber And Blue Blocker," the contents of which are incorporated herein by reference in their entirety.

FIELD OF THE INVENTION

This invention relates generally to ophthalmic lenses and, more specifically, to ophthalmic lenses comprising materials for blocking the transmission of certain light frequencies.

BACKGROUND OF THE INVENTION

Blue blocking (400-500 nm radiation) and violet blocking (400-440 nm) chromophores have been incorporated into plastics used as ophthalmic lenses (e.g. spectacles, intraocular lenses and contact lenses). Blue blocking and violet blocking agents are reported to protect the retina against damaging higher energy visible light radiation. Ultraviolet blocking agents are also added to ophthalmic lenses to protect the retina against UV-A radiation. Together, blue blocker and UV absorber, absorb the damaging radiation spectrum that can potentially reach the retina.

U.S. Pat. No. 5,470,932, for example, teaches against the use of vinyl-functionalized dyes in acrylate-based polymer systems, recommending the use of acrylate polymerizable groups. The inventor argues that yellow dyes having acrylate or methacrylate functional groups are more efficiently bound by covalent bonds into acrylate polymers than a dye that has vinyl functionality. An example of a vinyl polymerizable dye cited in this patent, i.e., 4-phenylazophenol allyl ether, suggests that the formulation of such dyes is inefficient, in that a 44% absorption loss is reported after soxhlet extraction in acetone.

Accordingly, there is a need for an ophthalmic lens light blocking system which avoids the aforementioned problem in the prior art.

SUMMARY OF THE INVENTION

The invention satisfies this need. The invention is a polymeric ophthalmic lens material comprising a) one or more lens-forming polymerizable monomers selected from the group of hydrophilic acrylate-substituted monomers, hydrophobic acrylate-substituted monomers, vinyl-substituted monomers, and platinum-catalyzed vinyl hydride addition-cured silicones, b) a polymerizable ultraviolet absorber and c) a polymerizable yellow dye.

In one embodiment of the invention, the polymerizable ultraviolet absorber has the formula:

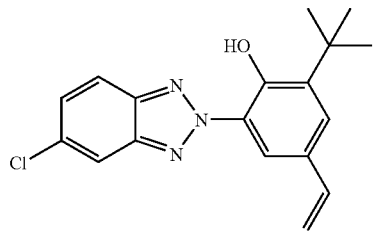 [SMILES: C=Cc1cc(-n2nc3ccc(Cl)cc3n2)c(O)c(C(C)(C)C)c1]

and the polymerizable yellow dye has the formula:

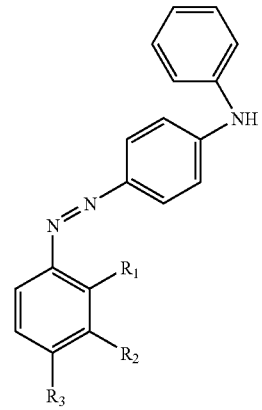

wherein $R_1$=vinyl, $R_2$, $R_3$=H, alkyl, hydroxyalkyl, wherein $R_2$=vinyl, $R_1$, $R_3$=H, alkyl, hydroxyalkyl, and wherein $R_3$=vinyl, $R_1$, $R_2$=H, alkyl, hydroxyalkyl.

As used in this application, the phrase "wherein $R_1$=vinyl, $R_2$, $R_3$=H, alkyl, hydroxyalkyl, wherein $R_2$=vinyl, $R_1$, $R_3$=H, alkyl, hydroxyalkyl, and wherein $R_3$=vinyl, $R_1$, $R_2$=H, alkyl, hydroxyalkyl" is meant to describe the different structures as summarized in the following table:

| Structure | R1 | R2 | R3 |
|---|---|---|---|
| 1 | Vinyl | H | H |
| 2 | Vinyl | H | alkyl, hydroxyalkyl |
| 3 | Vinyl | alkyl, hydroxyalkyl | H |
| 4 | vinyl | alkyl, hydroxyalkyl | alkyl, hydroxyalkyl |
| 5 | alkyl, hydroxyalkyl | Vinyl | H |
| 6 | H | vinyl | alkyl, hydroxyalkyl |
| 7 | alkyl, hydroxyalkyl | vinyl | alkyl, hydroxyalkyl |
| 8 | H | Vinyl | H |
| 9 | alkyl, hydroxyalkyl | H | Vinyl |
| 10 | H | alkyl, hydroxyalkyl | Vinyl |
| 11 | alkyl, hydroxyalkyl | alkyl, hydroxyalkyl | Vinyl |
| 12 | H | H | Vinyl |

DRAWINGS

Figure 2:
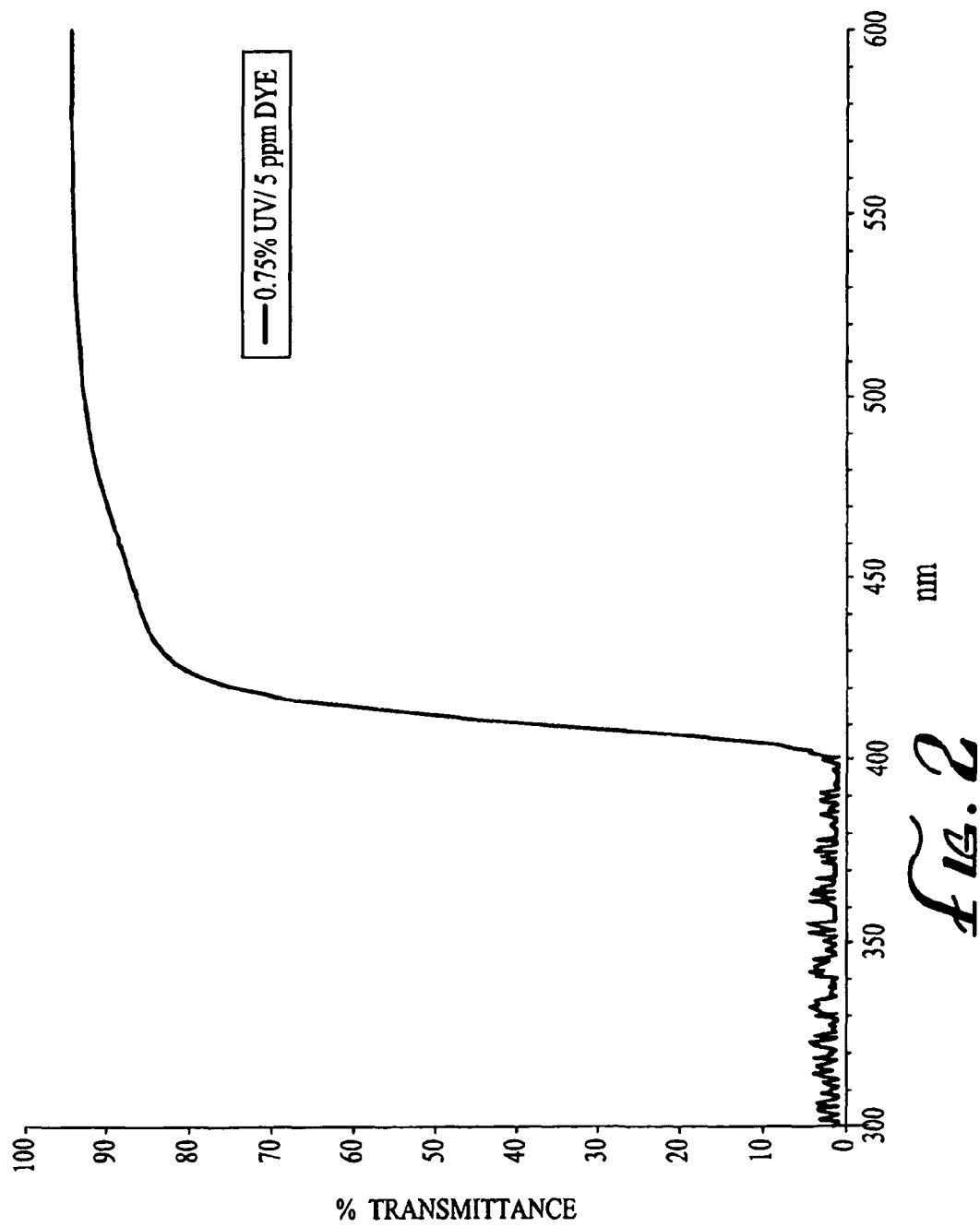

These and other features, aspects and advantages of the present invention will become better understood with reference to the following description, appended claims and accompanying drawings where:

FIG. 1 is a transmittance curve illustrating the blue blocking characteristics of a lens having features of the invention; and FIG. 2 is a transmittance curve illustrating the violet blocking characteristics of a lens having features of the invention.

DETAILED DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well.

The invention is a polymeric ophthalmic lens material comprising a) one or more lens-forming polymerizable monomers selected from the group of hydrophilic acrylate-substitute monomers, hydrophobic acrylate-substituted monomers, vinyl-substituted monomers, and platinum catalyzed vinyl hydride addition cured silicones, b) a polymerizable ultraviolet absorber and c) a polymerizable yellow dye.

Preferably, lenses made from the polymeric ophthalmic lens material of the invention are capable of blocking between about 40% and about 60%, preferably between about 50% and about 60%, of light having a wavelength of 450 nm.

In one embodiment of the invention, the polymerizable ultraviolet absorber has the formula:

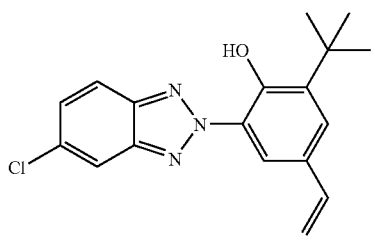 [SMILES: C=Cc1cc(-n2nc3ccc(Cl)cc3n2)c(O)c(C(C)(C)C)c1]

and the polymerizable yellow dye has the formula:

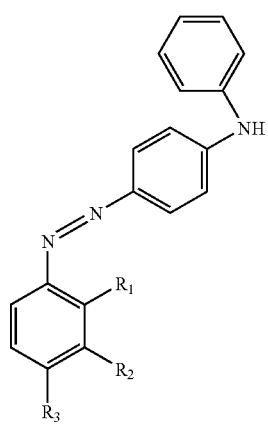

wherein $R_1$=vinyl, $R_2$, $R_3$=H, alkyl, hydroxyalkyl, wherein $R_2$=vinyl, $R_1$, $R_3$=H, alkyl, hydroxyalkyl, and wherein $R_3$=vinyl, $R_1$, $R_2$=H, alkyl, hydroxyalkyl.

The preparation of 2-(5-Chloro-2H-benzotriazol-2-yl)-6-(1,1-dimethylethyl)-4-ethenylphenol is described in U.S. Pat. No. 4,868,251.

The preparation of the yellow dye (N-phenyl-4-(3-vinylphenylazo)-aniline) is also easily accomplished using procedures known to those skilled in the art. For example, to prepare the 3 vinyl diazonium salt, 3-vinyl aniline is dissolved in glacial acetic acid acidified with sulfuric acid and the solution is chilled to 5° C. A pre-chilled aqueous solution of sodium nitrite is added dropwise to the vinyl aniline solution and the mixture is then stirred in an ice bath for 2.5 hours yielding a clear yellow solution of the 3-vinyl diazonium salt. This solution is then added dropwise to a pre-chilled (5° C.) methanol solution of diphenylamine solution. The reaction mixture is stirred overnight at room temperature. A dark purple fine suspension is formed. The solution is neutralized with sodium hydroxide, the raw product is collected as precipitate and redissolved in ether. The ether phase is first water washed and the raw product purified by silica gel column chromatography. The dye is recovered as an orange solid.

Typically, the concentration of the ultraviolet absorber is between about 0.1% and about 1.0% on a weight to weight basis. Typically, the concentration of the yellow dye is between about 10 ppm and about 500 ppm on a weight to weight basis.

One formulation of a blue blocking lens has about 0.5% of the ultraviolet absorber with about 50 ppm of the yellow dye. The transmittance curve of a 1 mm thick hydrophobic acrylic lens made with this blue blocking formula is provided in FIG. 1.

Another formulation of a violet blocking lens has about 0.75% of the ultraviolet absorber with 5 ppm of the yellow dye. The transmittance curve of a 1 mm thick hydrophobic acrylic lens made with this violet blocking formula is provided in FIG. 2.

Other typical formulations of the invention have yellow dye concentrations as summarized in the following table:

| Lens Thickness (mm) | Yellow Dye Conc Range min/max (ppm(w/w)) |
| --- | --- |
| 0.1 | 430/770 |
| 0.25 | 170/315 |
| 0.50 | 85/160 |
| 1.0 | 30/80 |

Thus, it can be seen that the unique combination of ultraviolet absorber and yellow dye permits the use of low concentrations to achieve the ultraviolet absorber requirement (>99% absorption of ultraviolet light of wavelengths less than 400 nm) and violet or blue blocking requirements. The total concentration of vinyl containing chromophore (ultraviolet absorber and yellow dye) is less than 0.5% in a blue blocking 1 mm thick hydrophobic acrylic lens with the transmittance curve in FIG. 1. The concentration of yellow dye is about 50 ppm. Thus, the invention constitutes a highly efficient and flexible light absorbing system for retinal protection. The absorption characteristics of the invention permit effective blue blocking capability in thin lenses, i.e. 0.25 mm, at practicable chromophore concentrations. At 0.25 mm, the total concentration of vinyl-containing chromophore would not exceed 1.2% and the yellow dye concentration would be less than 250 ppm.

The yellow dye is also covalently bound by a vinyl polymerizable group yet it undergoes only 0.5% absorption loss from the material described in the above example following soxhlet extraction. This loss is significantly less than even those reported for the two acrylate/acrylamide polymerizable preferred compounds disclosed in Jinkerson (i.e. N-2-[3-(2'-methylphenylazo)-4-hydroxylphenyl]ethylmethacrylamide and N-(4'-phenylazo)phenyl-2-bis-(2-methacrylo)ethy-lamine) where he reported absorption losses of 10% and 1%, respectively for these compounds. The extremely low losses of chromophore in material after soxhlet extraction in the example below are indicative of high levels of covalent coupling into the polymer. Efficient coupling of the dye is attributed to the extremely low dye concentrations that are needed to meet either blue blocking or violet blocking requirements of optical lenses of typical thicknesses ranging from 0.2 mm to 2 mm.

EXAMPLE

The following example describes the forming of one embodiment of the invention wherein a blue blocking acrylic material with 0.5 percent 2-(5-Chloro-2H-benzotriazol-2-yl)-6-(1,1-dimethylethyl)-4-ethenylphenol and 50 ppm 0.5% N-phenyl-4-(3-vinylphenylazo)-aniline:

Blue Blocking Transparent Foldable Acrylic (BBTFA) Polymer: The N-phenyl-4-(3-vinylphenylazo)-aniline and 2-(5-Chloro-2H-benzotriazol-2-yl)-6-(1,1-dimethylethyl)-4-ethenylphenol, respectively were polymerized with other monomers to produce the BBTFA material. Ethyl methacrylate (70.7 gms), butyl acrylate (137.7 grams), N-benzyl-N-isopropyl acrylamide (39.5 grams), ethylene glycol dimethacrylate (15.6 grams), azoisobutyronitrile (0.33 grams), 2-(5-chloro-2Hbenzotriazol-2-yl)-6-(1,1-dimethylethyl)-4-ethenylphenol (1.33 grams) and N-phenyl-4-(3-vinylphenylazo)-aniline (0.0133 grams) were mixed in a round bottom flask and deoxygenated with nitrogen gas for one hour. The liquid mixture was filtered and transferred into glass molds designed to produce 2 mm thick sheets. The glass molds were placed in a programmable oven and cured. The molds were rapidly heated to 60° C. and left at this temperature for sixteen hours, and were then heated to 140° C. and post cured for 8 hours. After demolding, buttons were cut from the sheet and lathed down to 1 mm thickness. The transmittance curve of the 1 mm thick sample is shown in FIG. 1.

Having thus described the invention, it should be apparent that numerous structural modifications and adaptations may be resorted to without departing from the scope and fair meaning of the instant invention as set forth hereinabove and as described herein below by the claims.

What is claimed is:

1. A polymeric ophthalmic lens comprising:
a) a polymerizable ultraviolet absorber; and
b) a polymerizable yellow dye;
wherein the ultraviolet absorber has the formula:

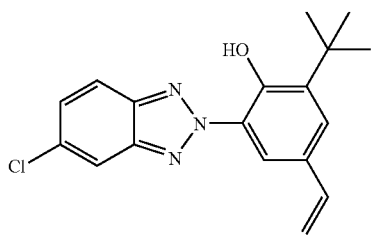 [SMILES: C=Cc1cc(-n2nc3ccc(Cl)cc3n2)c(O)c(C(C)(C)C)c1]

and the polymerizable yellow dye has the formula:

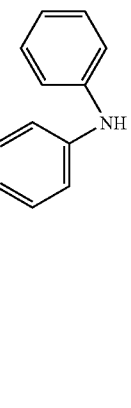

wherein, $R_1$=vinyl, $R_2$, $R_3$=H, alkyl, hydroxyalkyl, wherein $R_2$=vinyl, $R_1$, $R_3$=H, alkyl, hydroxyalkyl, and wherein $R_3$=vinyl, $R_1$, $R_2$=H, alkyl, hydroxyalkyl;

wherein the lens has an optical axis and a thickness measured along the optical axis of less than about 1.1 mm; and wherein the lens is capable of blocking between about 40% and about 60% of light having a wavelength of 450 nm and 99% of light having wavelengths less than 400 nm.

2. The polymeric ophthalmic lens of claim 1 wherein the lens has a thickness of about 1.0 mm and the concentration of the polymerizable yellow dye is between about 30 ppm and about 80 ppm on a weight to weight basis.

3. The polymeric ophthalmic lens of claim 1 wherein the lens is capable of blocking between about 50% and about 60% of light having a wavelength of 450 nm.

4. A polymeric ophthalmic lens comprising:
a) a polymerizable ultraviolet absorber; and
b) a polymerizable yellow dye;
wherein the ultraviolet absorber has the formula:

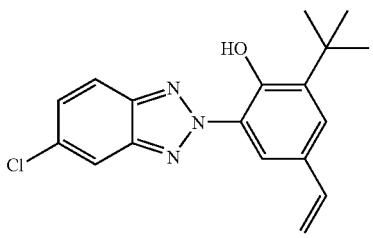 [SMILES: C=Cc1cc(-n2nc3ccc(Cl)cc3n2)c(O)c(C(C)(C)C)c1]

and the polymerizable yellow dye has the formula:

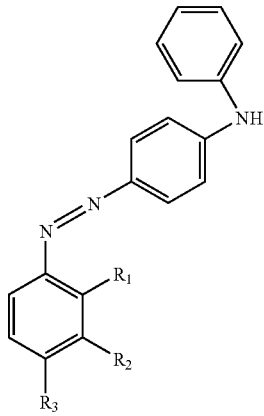

wherein, $R_1$=vinyl, $R_2$, $R_3$=H, alkyl, hydroxyalkyl, wherein $R_2$=vinyl, $R_1$, $R_3$=H, alkyl, hydroxyalkyl, and wherein $R_3$=vinyl, $R_1$, $R_2$=H, alkyl, hydroxyalkyl;

wherein the lens is capable of blocking between about 40% and about 60% of light having a wavelength of 450 nm and 99% of light having wavelengths less than 400 nm; and wherein the thickness of the lens measured along the optical axis of the lens is less than about 0.6 mm.

5. The polymeric ophthalmic lens of claim 4 wherein the thickness of the lens is about 0.5 mm and the concentration of the polymerizable yellow dye is between about 85 ppm and about 160 ppm on a weight to weight basis.

6. The polymeric ophthalmic lens of claim 4 wherein the thickness of the lens is about 0.25 mm and the concentration of the polymerizable yellow dye is between about 170 ppm and about 315 ppm on a weight to weight basis.

7. The polymeric ophthalmic lens of claim 4 wherein the lens is capable of blocking between about 50% and about 60% of light having a wavelength of 450 nm.

8. A polymeric ophthalmic lens comprising:
a) a polymerizable ultraviolet absorber; and
b) a polymerizable yellow dye;
wherein the ultraviolet absorber has the formula:

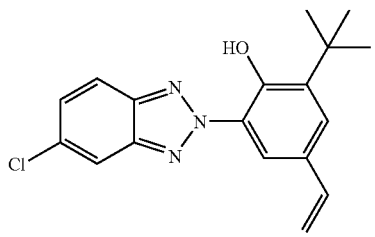 [SMILES: C=Cc1cc(-n2nc3ccc(Cl)cc3n2)c(O)c(C(C)(C)C)c1]

and the polymerizable yellow dye has the formula:

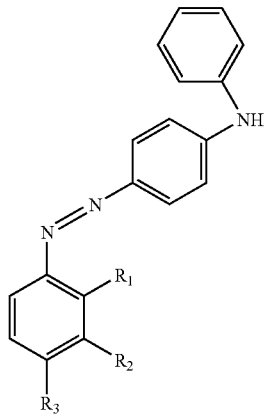

wherein, $R_1$=vinyl, $R_2$, $R_3$=H, alkyl, hydroxyalkyl, wherein $R_2$=vinyl, $R_1$, $R_3$=H, alkyl, hydroxyalkyl, and wherein $R_3$=vinyl, $R_1$, $R_2$=H, alkyl, hydroxyalkyl;

wherein the lens is capable of blocking between about 40% and about 60% of light having a wavelength of 450 nm and 99% of light having wavelengths less than 400 nm; and wherein the thickness of the lens measured along the optical axis of the lens is less than about 0.2 mm.

9. The polymeric ophthalmic lens of claim 8 wherein the lens is capable of blocking between about 50% and about 60% of light having a wavelength of 450 nm.

10. A polymeric ophthalmic lens comprising:
a) a polymerizable ultraviolet absorber; and
b) a polymerizable yellow dye;
wherein the polymerizable yellow dye has the formula:

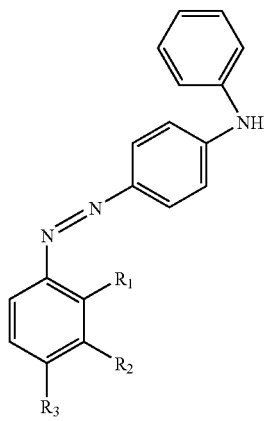

wherein, $R_1$=vinyl, $R_2$, $R_3$=H, alkyl, hydroxyalkyl, wherein $R_2$=vinyl, $R_1$, $R_3$=H, alkyl, hydroxyalkyl, and wherein $R_3$=vinyl, $R_1$, $R_2$=H, alkyl, hydroxyalkyl;

wherein the lens is capable of blocking between about 40% and about 60% of light having a wavelength of 450 nm and 99% of light having wavelengths less than 400 nm; and wherein the thickness of the lens measured along the optical axis of the lens is less than about 0.2 mm.

11. The polymeric ophthalmic lens of claim 10 wherein the thickness of the lens is about 0.1 mm and the concentration of the polymerizable yellow dye is between about 430 ppm and about 770 ppm on a weight to weight basis.

12. A polymeric ophthalmic lens comprising:

a) one or more lens-forming polymerizable monomers selected from the group of lens-forming polymerizable monomers consisting of hydrophilic acrylate-substituted monomers, hydrophobic acrylate-substituted monomers, vinyl-substituted monomers, and platinum-catalyzed vinyl hydride addition-cured silicones;

b) a polymerizable ultraviolet absorber having the formula:

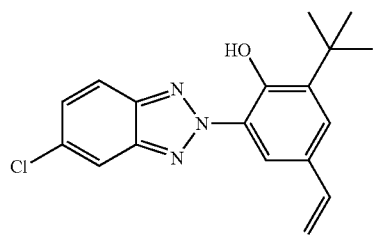 [SMILES: C=Cc1cc(-n2nc3ccc(Cl)cc3n2)c(O)c(C(C)(C)C)c1]

and c) a polymerizable yellow dye having the formula:

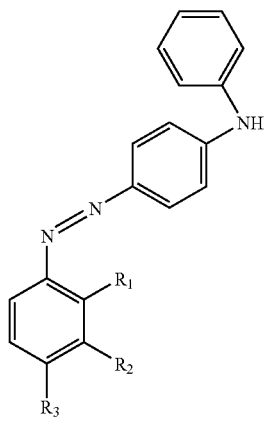

wherein, $R_1$=vinyl, $R_2$, $R_3$=H, alkyl, hydroxyalkyl, wherein $R_2$=vinyl, $R_1$, $R_3$=H, alkyl, hydroxyalkyl, and wherein $R_3$=vinyl, $R_1$, $R_2$=H, alkyl, hydroxyalkyl.

* * * * *